United States Patent [19]

Shirasaki et al.

[11] Patent Number: 5,323,782
[45] Date of Patent: Jun. 28, 1994

[54] ELECTRONIC BLOOD PRESSURE METER

[75] Inventors: Osamu Shirasaki, Hyogo; Masashi Fukura; Akihiro Sasabata, both of Kyoto; Yoshinori Miyawaki, Shiga, all of Japan

[73] Assignee: Omron Corporation, Kyoto, Japan

[21] Appl. No.: 836,651

[22] Filed: Feb. 18, 1992

[30] Foreign Application Priority Data

Feb. 15, 1991 [JP] Japan .................................. 3-22271
Feb. 18, 1991 [JP] Japan .................................. 3-23065

[51] Int. Cl.$^5$ .............................................. A61B 5/00
[52] U.S. Cl. .................................... 128/680; 128/681; 364/413.03
[58] Field of Search ............................... 128/677–686

[56] References Cited

U.S. PATENT DOCUMENTS

| | | | |
|---|---|---|---|
| 3,814,083 | 6/1974 | Fletcher et al. | 128/2.05 A |
| 4,312,359 | 1/1982 | Olson | 128/680 |
| 4,427,013 | 1/1984 | Nunn et al. | |
| 4,534,361 | 8/1985 | Berger et al. | 128/680 |
| 4,830,019 | 5/1989 | Shirasaki et al. | 128/681 |
| 4,872,461 | 10/1989 | Miyawaki | 128/682 |
| 4,917,098 | 4/1990 | Murase | 128/681 |

FOREIGN PATENT DOCUMENTS

| | | |
|---|---|---|
| 0029166 | 5/1981 | European Pat. Off. . |
| 0266444 | 11/1986 | European Pat. Off. . |
| 0249990 | 12/1987 | European Pat. Off. . |
| 0332701 | 7/1990 | European Pat. Off. . |
| 0379996 | 8/1990 | European Pat. Off. . |
| 3143372 | 5/1983 | Fed. Rep. of Germany . |
| 3424535 | 1/1986 | Fed. Rep. of Germany . |

OTHER PUBLICATIONS

European Search Report dated Jul. 9, 1993.

*Primary Examiner*—Kyle L. Howell
*Assistant Examiner*—Robert L. Nasser, Jr.
*Attorney, Agent, or Firm*—Fish & Richardson

[57] ABSTRACT

An electronic blood pressure meter capable of performing a proper automatic pressuring operation according to a blood pressure of a subject and measuring the blood pressure rapidly with accuracy. An electronic blood pressure meter includes a cuff, a pressure controller for controlling an inside fluid pressure of the cuff, a pressure sensor for sensing the inside fluid pressure of the cuff to produce a cuff pressure detecting signal, an extracting unit for extracting a pulse wave component superposed on the cuff pressure detecting signal during pressure control operations performed by the pressure controller, a calculating unit for calculating an amplitude of the extracted pulse wave for each pressure measurement, a unit for determining a blood pressure during an evacuating operation of the pressure controller based on output signals from the calculating unit and the pressure sensor, maximum blood pressure estimating unit which obtains an estimated value of a maximum blood pressure in response to output signals from the extracting unit and the pressure sensor during the pressuring operation of the control means. The pressure controller stops the pressuring operation when the inside fluid pressure of the cuff exceeds a total pressure of the estimated value and a predetermined value.

3 Claims, 10 Drawing Sheets

ELECTRONIC BLOOD PRESSURE METER

BACKGROUND OF THE INVENTION

The present invention relates to an electronic blood pressure meter capable of performing an automatic pressuring operation according to the blood pressure of a subject and measuring the blood pressure rapidly with accuracy.

An electronic blood pressure meter includes a cuff, a pump for pressuring the cuff, an evacuation valve for evacuating the cuff, a pressure sensor for detecting a cuff pressure, and a microcomputer (MPU).

The MPU includes the functions of calculating a pulse wave amplitude value from the pulse wave component detected from an output signal of the pressure sensor, and determining a maximum blood pressure value (SYS) and a minimum blood pressure value (DIA) from the cuff pressure and the pulse wave amplitude value. The electronic blood pressure meter generally adopts a threshold technique in determining the blood pressure value. When making measurements, the cuff is pressured to check the flow of blood in the artery, and then pulse wave amplitude values incorporated in the cuff pressure are detected during the evacuation process. The pulse wave is a volumetric variation of the artery caused when the blood starts flowing during the process of evacuating the cuff at a slow speed. This volumetric variation is transmitted to the cuff and thus detected. The pulse wave amplitude value depicts a curve (an envelope) that gradually increases as the cuff pressure decreases, reaches a maximum, and then tends to decrease temporarily. Here, the maximum pulse wave amplitude value is detected, and during the phase in which the pulse wave amplitude increases, the pulse wave amplitude value closest to the threshold, which is the predetermined percentage of the maximum pulse wave amplitude value (e.g., 50% of the maximum pulse wave amplitude value), is detected, and the maximum blood pressure value is set to the cuff pressure at this point. Further, during the phase in which the pulse wave amplitude decreases, the pulse wave amplitude value closest to another threshold, which is a predetermined percentage of the maximum pulse wave amplitude value (e.g., 70% of the maximum pulse wave amplitude value), is detected, and the minimum blood pressure value is set to the cuff pressure at this point.

The electronic blood pressure meter pressures the cuff to a target pressuring value (a pressuring value above the maximum blood pressure value) to stop the flow of blood in the artery, obtains thereafter a cuff pressure and pulse wave information during the process of evacuating the cuff at a predetermined low speed (4 mmHg/s), and determines a blood pressure based on the cuff pressure and the pulse wave information.

Oscillometric electronic blood pressure meters track a pulse wave superposed on a cuff pressure and calculate a blood pressure based on a change in the amplitude of the pulse wave. The amplitude is, as shown in FIG. 1, small when the cuff pressure is sufficiently large with respect to a systolic pressure (a maximum blood pressure), increases as the cuff is being evacuated thereafter, and maximizes immediately before the cuff pressure becomes equal to a diastolic pressure (a minimum blood pressure). It is assumed that the cuff pressure becomes substantially equal to the average blood pressure. It maximizes at a maximum pulse wave point P. The amplitude decreases thereafter. The blood pressure is calculated based on this change in amplitude.

In an oscillometric method in which the blood pressure is calculated based on this amplitude variation, an entire amplitude change pattern (an envelope) is required. For example, according to a technique, a systolic pressure (the maximum blood pressure) and a diastolic pressure (the minimum blood pressure) are calculated as points S and D at which the pulse waves become equal to certain values on the higher pressure side and on the lower pressure side than the maximum points (points P), respectively, the certain values being obtained by multiplying the maximum values by certain percentages. More specifically, the blood pressure cannot be calculated unless all the points, S, P, and D, on the envelope are tracked. To track these three points means, it is necessary to pressure the cuff to a value larger than the point S before starting a measuring operation. If a cuff pressure larger than the point S is not obtained, the absence of the point S is discovered when the point P is detected in the blood pressure measurement operation, which makes the measurement unsuccessful due to failure to calculate the systolic pressure (the maximum blood pressure). Therefore, the user must repeat the pressuring operation at a pressure higher than in the last pressuring operation and make a measurement again. Since the point S (systolic pressure) is unknown to the user and it is very difficult to set the pressuring operation properly by estimating this point when a subject is has hypertension causing the blood pressure to undergo a noticeable variation. Further, if a measurement has been unsuccessful, it takes time to complete the measurement. Hence, a conventional practice is that the pressuring value is set to a point higher than necessary, which often keeps a subject under pain disadvantageously. For these reasons, a function of automatically setting the pressuring value has been called for.

In the above-mentioned conventional electronic blood pressure meter, the pulse wave amplitude is tracked during the cuff pressuring process in which the cuff is being pressured for a predetermined time and at a predetermined pressuring speed as shown in FIG. 2. If a plurality of pulse wave amplitudes sufficient to allow a maximum blood pressure to be estimated, can be obtained during the pressuring process, a maximum blood pressure can be estimated by applying a predetermined algorithm, and by stopping the cuff pressuring operation when the cuff pressure reaches an ideal pressuring target. An ideal pressuring target can be obtained by adding a predetermined pressure to the estimated maximum blood pressure. However, as shown in FIG. 3, for example, if an arm is thin, the cuff pressuring speed may become too fast. In such a case, if the pressuring speed is not variable as in the conventional system, a part of the pulse wave is missed no matter how many times the cuff pressuring operations are repeated. As a result, pulse wave information needed to determine a maximum blood pressure cannot be obtained. Thus, no maximum blood pressure is estimated. Therefore, the disadvantage that no proper pressuring target can be determined exists.

Since the predetermined slow evacuation is effected during a measurement in this blood pressure measuring system, it takes time to complete the measurement. As a result, the subject must endure pressure from the cuff for a long time, and the measurement may be painful to the subject. Particularly, a hypertensive subject must endure a slow evacuation process in which a large pressure is applied to the cuff. The evacuation process is so long that the subject feels numbness in his arm or gets some congestion at the artery, etc.

SUMMARY OF THE INVENTION

In view of the above, an object of the invention is to overcome the above problems and to provide an electronic blood pressure meter capable of reducing the measurement time and entailing less pain to a subject. The electronic blood pressure meter is also capable of tracking a pulse wave during the cuff pressuring process, calculating a maximum blood pressure easily as well as quickly, and performing the automatic setting of a pressuring operation.

The present invention provides an electronic blood pressure meter comprising a cuff, means for controlling an inside fluid pressure of the cuff, means for detecting the inside fluid pressure of the cuff to produce a cuff pressure detecting signal, means for extracting a pulse wave component superposed on the cuff pressure detecting signal during pressure control operations performed by the cuff pressure control means, means for calculating an amplitude of the extracted pulse wave every pressure, means for determining a blood pressure during an evacuating operation of the control means based on output signals of the amplitude calculating means and the pressure detecting means and maximum blood pressure estimating means for obtaining an estimated value of a maximum blood pressure in response to output signals of the pulse wave extracting means and pressure detecting means during a pressuring operation of the control means, the control means stopping the pressuring operation when the inside fluid pressure of the cuff exceeds the total pressure of the estimated value and a predetermined value.

BRIEF DESCRIPTION OF THE DRAWINGS

In the accompanying drawings.

DESCRIPTION OF THE PREFERRED EMBODIMENTS

Figure 1:
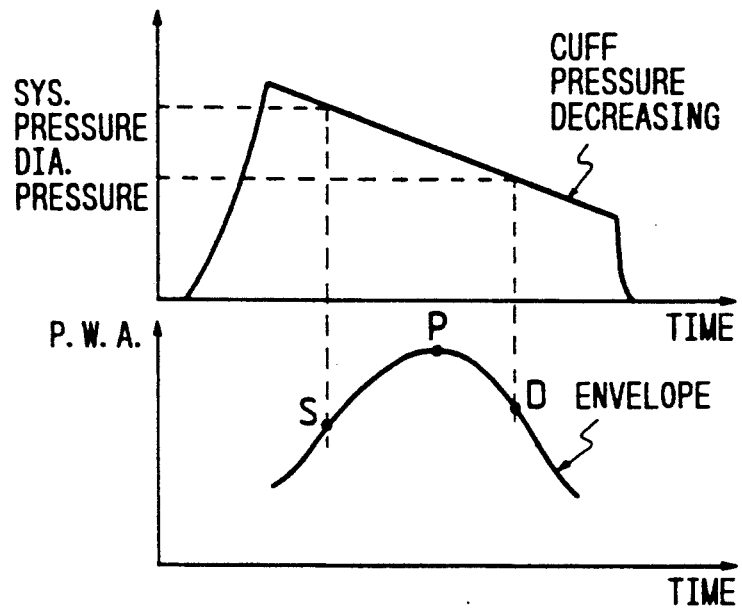
FIG. 1 is a diagram illustrative of a blood pressure determining process in an oscillometric blood pressure meter.
Figure 2:
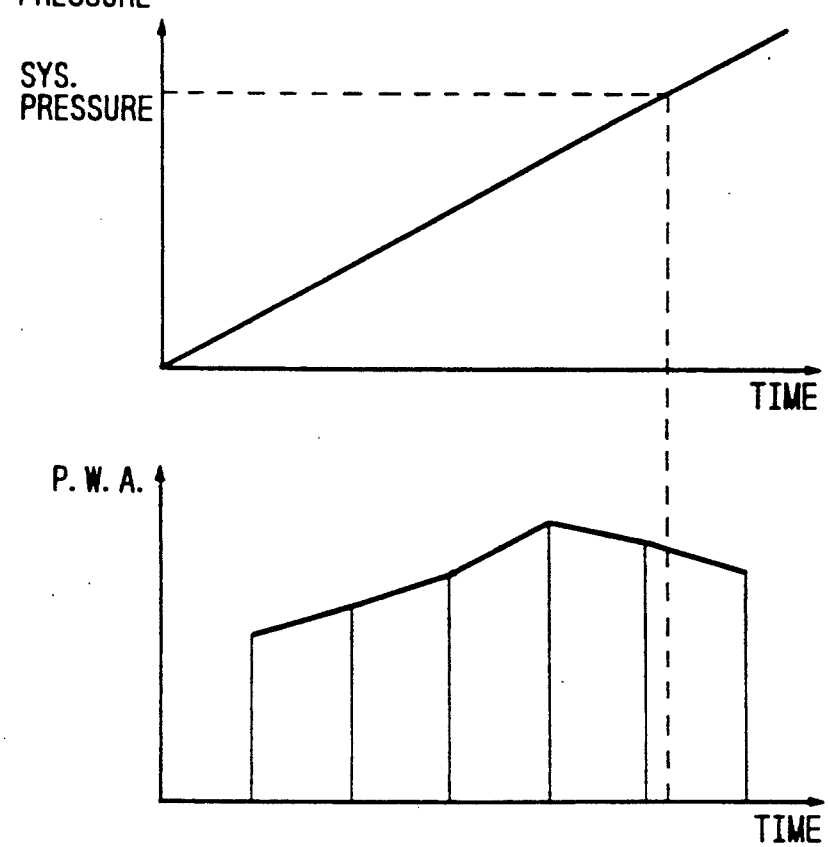
FIG. 2 is a diagram illustrative of a case in which a maximum blood pressure can be estimated because the pressuring speed is appropriate.
Figure 3:
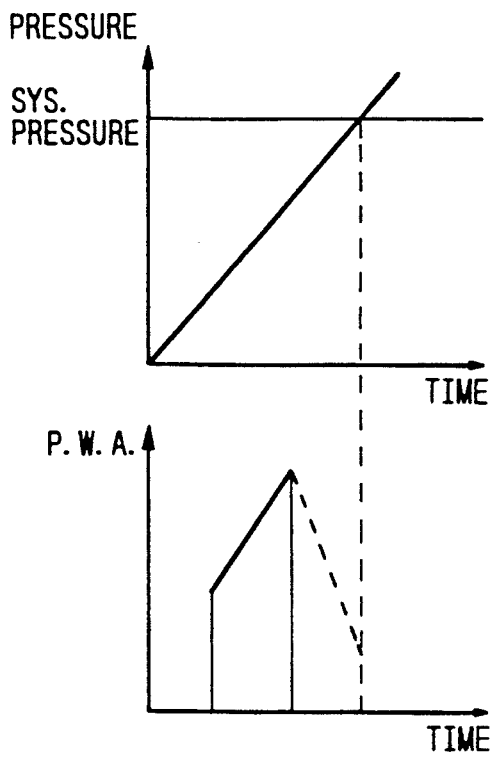
FIG. 3 is a diagram illustrative of a case in which a maximum blood pressure cannot be estimated because the pressuring speed is too fast.
Figure 4:
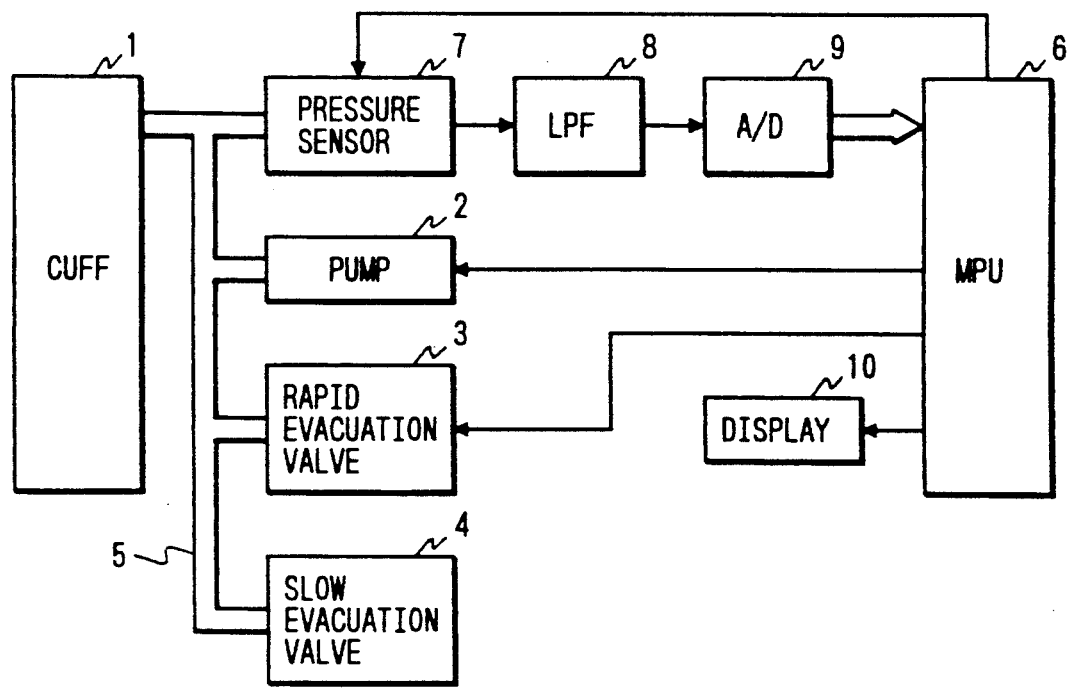
FIG. 4 is a block diagram showing a circuit configuration of the electronic blood pressure meter.

FIG. 4 is a circuit block diagram showing an electronic blood pressure meter.

The electronic blood pressure meter includes a cuff 1, a pressuring pump 2 for pressuring the cuff 1, a rapid evacuation valve 3 for decreasing the internal pressure of the cuff, and a slow evacuation valve 4. These components are connected to each other through an air tube 5 to form an air system. The rapid evacuation valve 3 and the pressuring pump 2 are electrically connected to an MPU 6 to be described later, and controlled by the MPU 6 independently. Further, a pressure sensor 7 is connected to the air tube 5. The pressure sensor 7 is, for example, a diaphragm converter using a strain gauge, or a semiconductor pressure conversion element. An analog output signal from the pressure sensor 7 is sent through a lowpass filter 8 to be converted into a digital signal by the A/D converter 9. The lowpass filter 8 removes pressure noise from the pressuring pump 2 that may have been introduced to the cuff pressure signal when detecting a pulse wave during the pressuring process. The cut-off frequency of the lowpass filter 8 is within the range of 10 to 30 Hz. The MPU 6 periodically receives a digital, noiseless output signal from the pressure sensor 7. This MPU 6 includes a function for extracting pulse waves (tracking a pulse wave from cuff pressure data), a function for calculating a pulse wave amplitude (calculating a pulse wave amplitude by recognizing the start and end points of a pulse wave every pressure), and a function for calculating a blood pressure (calculating maximum and minimum blood pressure values from the pulse wave amplitudes, i.e., an envelope, obtained). Further, the MPU 6 has a function for calculating a threshold for determining a systolic pressure based on a maximum pulse wave during a cuff pressuring operation. The threshold is a value equal to 50% of a maximum pulse wave Amax. The MPU 6 also determines an estimated maximum blood pressure by judging whether or not the pressured pulse wave is smaller than the threshold, determines, as the estimated maximum blood pressure, the cuff pressure at the time the pressured pulse wave is smaller than the threshold, sets a pressuring operation by calculating an appropriate pressuring value based on the estimated maximum blood pressure, and stops the cuff pressuring operation when the cuff pressure equals the calculated pressure value. The MPU 6 also displays the determined maximum and minimum blood pressure values on a display 10.

Figure 5:
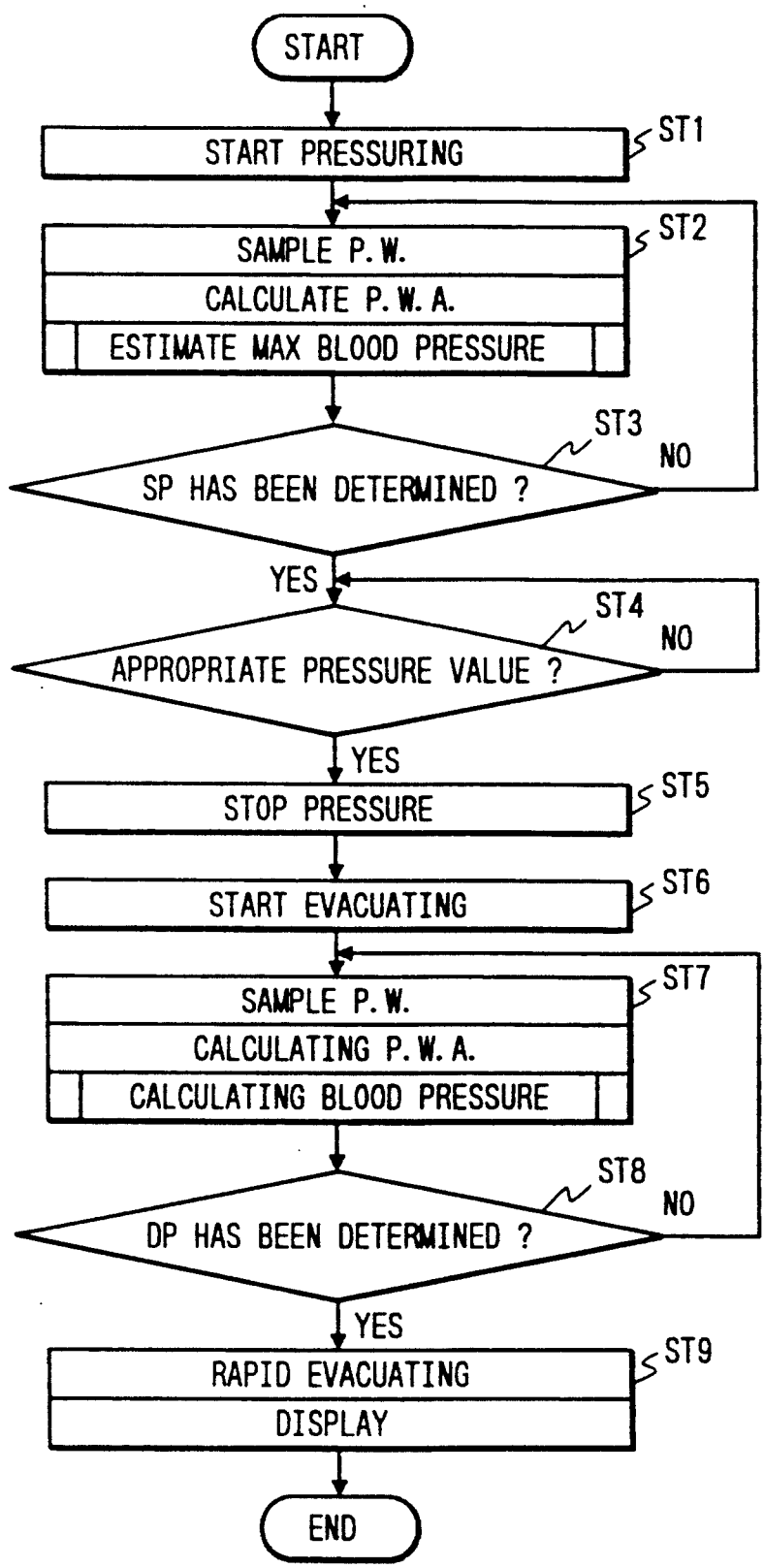
FIG. 5 is a main flowchart showing a specific operation of an electronic blood pressure meter, according to a first embodiment of the invention.

FIG. 5 is a flowchart showing a specific operation of an electronic blood pressure meter. When making a measurement, since both the power switch and the pressuring switch have been turned on, a pressuring operation of the cuff 1 is started [Step 1 (the word "Step" will hereinafter be referred to simply as "ST"]. During this cuff pressuring operation, pulse waves are read based on an output signal of the pressure sensor 7 and a pulse wave amplitude is calculated by recognizing the start and end points of each pulse wave for each pressure measurement. Further, a maximum blood pressure is estimated from the obtained pulse wave envelope (ST 2). In ST 3, it is determined whether or not the estimated maximum blood pressure (SP) has been calculated. If the cuff pressure does not adequately increase and the systolic pressure (SP) has not yet been determined, then the result in ST 3 is "NO," which causes the MPU 6 to return to ST 2. If the systolic pressure (ST) has been determined, then the result in ST 3 is "YES", which causes the MPU 6 to proceed to ST 4. In ST 4, a determination whether or not the cuff pressure has reached an appropriate pressuring value is made. That is, a determination is made whether or not the current pressure of the cuff I being pressured equals an appropriate pressuring value which is the estimated systolic pressure. Here, the term "appropriate pressuring value" means a value that is neither greater than nor less than the estimated systolic pressure. More specifically, the appropriate pressuring value is set by adding a predetermined value, e.g., 30 mmHg, to the estimated systolic pressure, taking into account systolic pressure estimating errors and a pressure drop between pressuring stop and measuring start. If it is assumed that the cuff pressure is not equal to the appropriate pressuring value, then the result in ST 4 becomes "NO," which causes the MPU to continue pressuring so that the appropriate pressuring value is obtained. As the cuff pressure reaches the appropriate pressuring value, the result in ST 4 becomes "YES," which causes the MPU 6 to stop driving of the pressuring pump 2 (ST 5), a slow evacuation of the cuff 1 begins, and a measurement is taken (ST 6). During this slow evacuation process, a pulse wave is extracted, a pulse wave amplitude is calculated, and a blood pressure is calculated as in the pressuring operation (ST 7). In ST 8, it is judged whether or not a minimum blood pressure DP (including the maximum blood pressure) has been calculated. This processing continues until the maximum and minimum blood pressure values are calculated in the slow cuff evacuation process, and when the diastolic pressure (the minimum blood pressure) has been determined, the result in ST 8 becomes "YES," which causes the MPU to rapidly evacuate the cuff 1 and display the measured blood pressure on the display 10 (ST 9).

Figure 6:
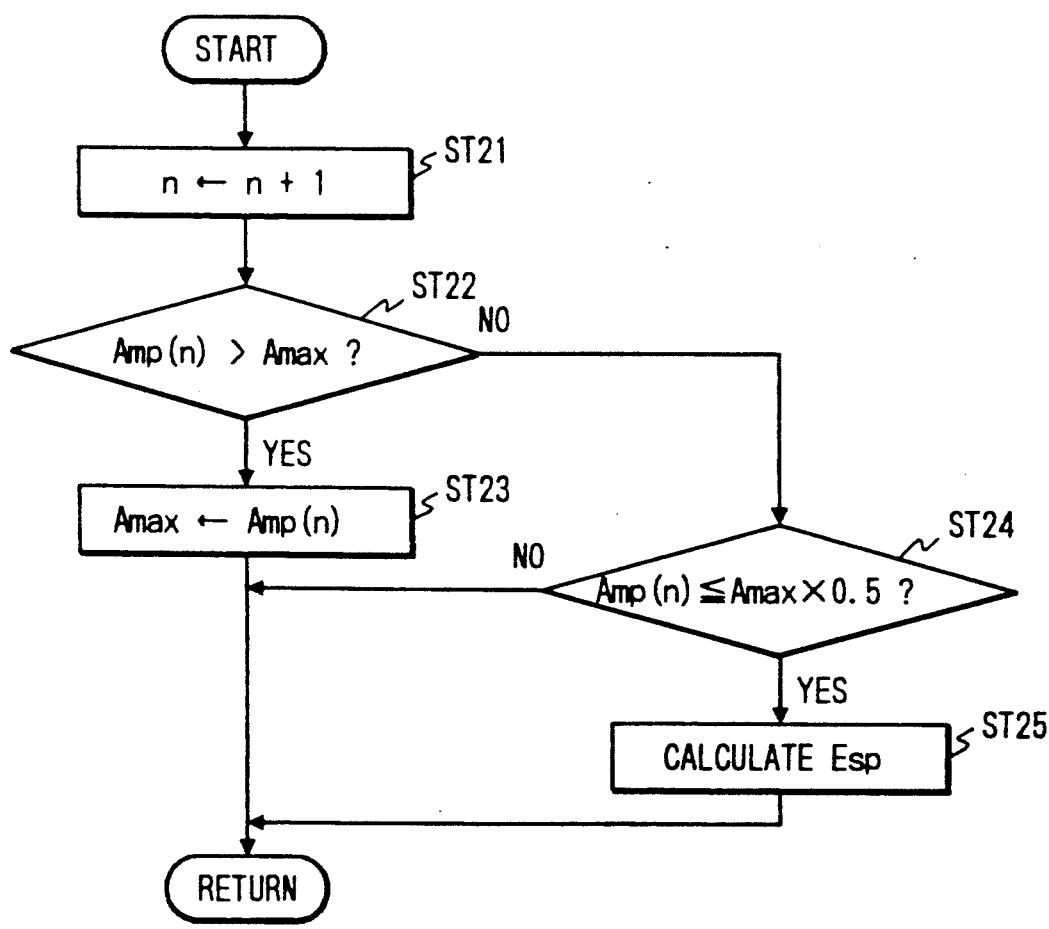
FIG. 6 is a flowchart showing a blood pressure estimating process during pressuring in the electronic blood pressure meter.

FIG. 6 is a flowchart showing a detailed operation of the blood pressure estimating processing (ST 2) performed during the pressuring operation.

Here, reference character (n) in a pulse wave amplitude AMP (n) designates a pulse wave number. It is assumed that the AMP (n) and a cuff pressure PC (n) have already been calculated by the pulse wave amplitude calculation processing that was performed before this blood pressure estimating processing. Further, the number (n) of a pulse wave and a variable Amax for storing the maximum pulse wave amplitude is initialized to "0" at the start of measuring. First, when the number n of a pulse wave is updated (ST 21), the pulse wave amplitude AMP (n) is compared with the maximum pulse wave amplitude Amax (ST 22). If AMP (n) is larger than Amax at this point, judging that the pulse wave envelope increasing (i.e., the pulse wave has not yet reached its maximum, the result is "YES," which causes the MPU to substitute the AMP (n) for the Amax (ST 23) and return thereafter. Later as AMP (n) becomes smaller than Amax, the result in ST 22 is "NO." The pulse wave envelope has passed its maximum point, and this causes the MPU 6 to determine that the envelope is decreasing, which causes the MPU to move onto ST 24. In ST 24, a determination of whether or not AMP (n) is less than the threshold for determining the systolic pressure. (The threshold is set to 0.5×Amax in this embodiment). If AMP (n) is not less than the threshold, then the result in ST 24 is "NO," which causes the MPU to return to ST 21. However, if AMP (n) is less than the threshold, the result in ST 24 is "YES," which causes the MPU to calculate an estimated systolic pressure (an estimated maximum blood pressure) Esp (ST 25). During the pressuring operation, the cuff pressure changes greatly and the pressure interval between pulse waves is large. Thus, if the cuff pressure when the pulse wave amplitude is less than the threshold is used as an estimated value, the accuracy of its measurements is questionable. To overcome this problem, Esp is calculated by extrapolation using the following equation.

$$\text{Esp} = \text{Pc}(n) + \frac{\text{THs} - \text{AMP}}{\text{AMP}(n-1) - \text{AMP}(n)} \times [\text{Pc}(n) - \text{Pc}(n-1)]$$

where THs is the threshold. After calculating the estimated pressuring value, the MPU 6 returns.

Figure 7:
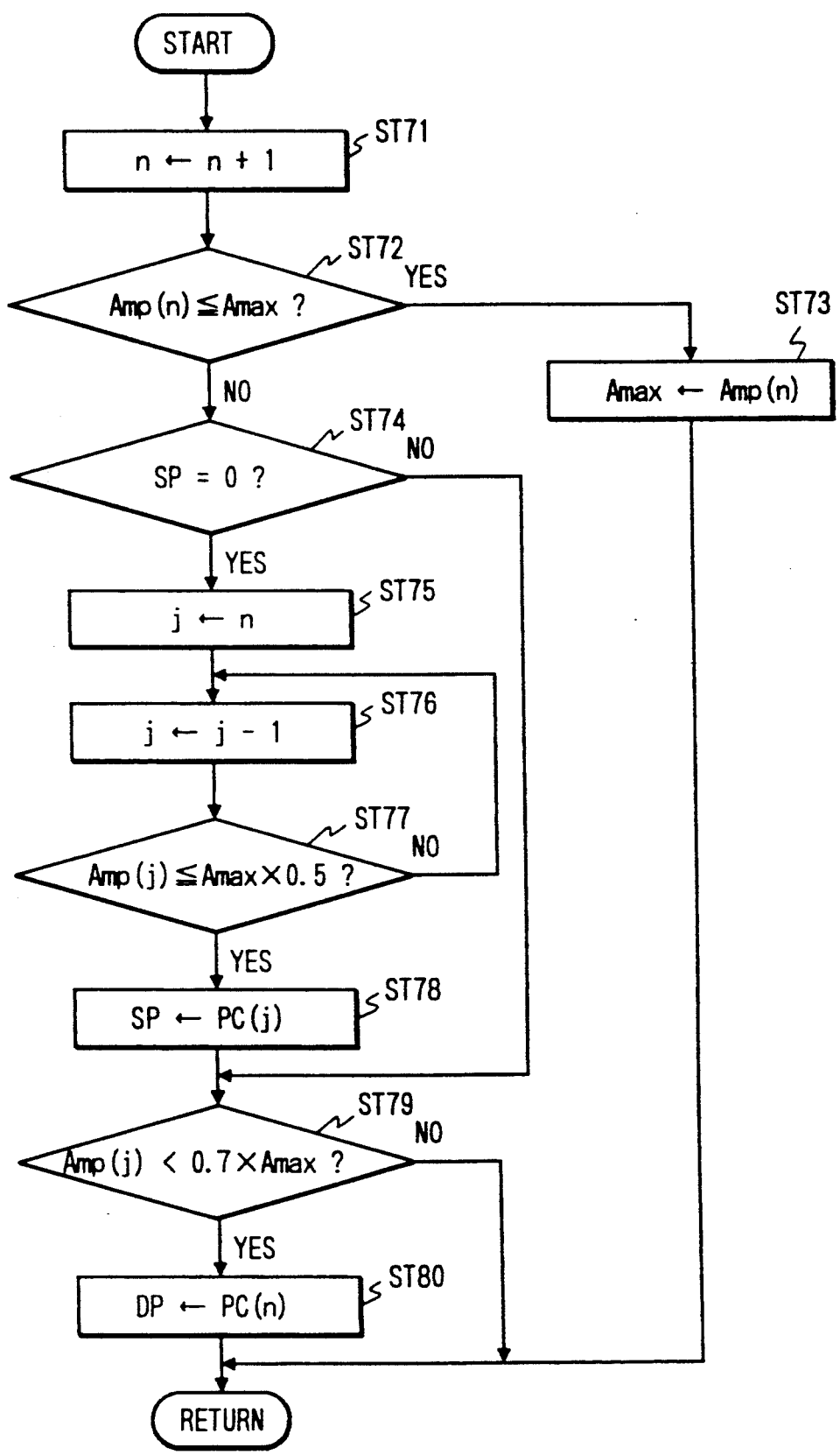
FIG. 7 is a flowchart showing a blood pressure calculating process during evacuating in the electronic blood pressure meter.

FIG. 7 is a flowchart showing a detailed operation of the blood pressure calculation processing (ST 7) performed during the evacuation process.

It is assumed that required data such as AMP (n) and PC(n) have already been calculated in the pulse wave extraction processing and pulse wave amplitude calculation processing performed immediately before this blood pressure calculation processing. It is also assumed that the number n of a pulse wave and a systolic pressure SP as well as a diastolic pressure DP have already been initialized to "0."

First, the number n of a pulse wave is incremented by 1 (ST 71). Then in ST 72, AMP (n) is compared with Amax. If AMP (n) is smaller than Amax, supposing that the pulse wave envelope has not reached its maximum point, the result in ST 72 is "YES," which causes the MPU to substitute AMP (n) for Amax (ST 73) and return to ST 71. If, on the other hand, AMP (n) is larger than Amax, the result in ST 72 is "NO," which causes the MPU to advance to ST 74. When AMP (n) is larger than Amax, it means that the envelope has passed its maximum point and is decreasing. In ST 74, a determination whether or not the systolic pressure (the maximum blood pressure) SP equals "0" is made. At this point if SP equal "0", SP has not yet been determined. In this case, the result in ST 74 is "YES," and the MPU thus performs the SP calculation processing in ST 75 through ST 78. Conversely, if SP has been determined, the result in ST 74 is "NO," and the MPU moves to ST 79 to execute the DP calculation processing. If it is assumed now that SP is "0" and thus not determined, then a pulse wave counter j is set to the current pulse wave number in ST 75 (ST 75). Then, the counter j is incremented by 1 (ST 76), and a pulse wave amplitude AMP (j) specified by j is compared with a maximum Amax×0.5 (ST 77). Here, if AMP (j) is larger than Amax×0.5, then the result in ST 77 is "NO," causing the MPU to return to ST 76. On the other hand, if AMP (j) is smaller than Amax×0.5, then PC (j) is considered the systolic pressure (the maximum blood pressure (SP (ST 78). The MPU advances to the diastolic pressure DP calculation processing. First, a determination whether or not AMP (n) is less than the threshold (AMP×0.7) in ST 79 is made. If AMP (n) is less than Amax×0.7, the result in ST 79 is "YES," which causes the MPU to recognize PC (n) as a DP (ST 80) and then return.

As described above, the invention detects the maximum pulse wave amplitude extracted during a cuff pressuring operation to calculate a threshold. Then, by determining whether or not the pulse wave amplitude during the pressuring operation is smaller than the threshold, the cuff pressure, when the pulse wave amplitude during the pressuring operation is less than the threshold, is the estimated maximum blood pressure, and the cuff pressuring operation ends when the cuff pressure is further increased by a predetermined pressure value with respect to the estimated maximum blood pressure. Thus, by extracting a pulse wave component during the cuff pressuring operation and estimating the systolic pressure based on the extracted pulse wave signal, the cuff pressuring operation can automatically be stopped at a cuff pressure that is neither greater than nor less than the blood pressure. As a result, the first embodiment of the invention can provide the advantages of improving the operability as well as quick measurement, pain reduction during measurement, and decreased cost.

The second embodiment of the invention will be described with reference to FIGS. 4, 8 and 9.

As in the first embodiment, the second embodiment of the electronic blood pressure meter includes a cuff 1, a pressuring pump 2 for pressuring the cuff, a rapid evacuation valve 3 for evacuating the cuff, and a slow evacuation valve 4, connected together by an air tube 5 to form an air system. This rapid evacuation valve 3 and the pressuring pump 2 are electrically connected to an MPU 6 to be described later, and controlled by the MPU 6 independently. Further, a pressure sensor 7 for detecting the pressure inside the cuff is connected to the air tube 5. The pressure sensor 7 detects the air pressure inside the cuff 1, sends the detection signal to an A/D converter 9 through a lowpass filter 8, and the A/D converter 9 converts this analog signal into a digital signal and transmits the digital signal to the MPU 6. This electronic blood pressure meter uses an oscillometric system as a blood pressure determining means in which the arterial wall pressed by the cuff I vibrates in accordance with the pulses. The amplitude of this vibration varies in accordance with the magnitude of the pressure. And this vibration causes the air pressure within the cuff I to vibrate through the cuff 1. The vibration of the air pressure within the cuff 1 is detected as a pulse wave. That is, a pulse wave that can be carried on the cuff pressure signal detected by the pressure sensor 7 is extracted to calculate a pulse wave amplitude value. The MPU 6 determines a maximum blood pressure value and a minimum pressure value by applying a predetermined known algorithm to the tracked pulse wave information. The MPU 6 also performs the function of executing a maximum blood pressure estimating process and determining as a pressuring target a cuff pressure defined by adding a predetermined pressure value (e.g., 15 mmHg) to the estimated maximum blood pressure. Further, the MPU 6 has not only the function of judging whether or not pulse wave information required for estimating the maximum blood pressure at the time the cuff 1 is being pressured for a predetermined time and at a predetermined pressuring speed has been obtained, but also the function of stopping the cuff 1 pressuring operation to rapidly evacuate the cuff 1 to such an extend that the cuff pressure is decreased to, e.g., 30 mmHg, and estimating a maximum blood pressure and determining the pressuring target by repressuring the cuff after the cuff pressuring speed is decreased to 70% of a predetermined pressuring speed in the case where it is judged that no pulse wave information required for estimating the maximum blood pressure has been obtained even if the cuff pressure has already reached, e.g., a level of 180 mmHg as shown in FIG. 9. The MPU 6 also performs the function of displaying the maximum blood pressure value and the minimum blood pressure value determined during the cuff evacuation process on a display 10.

Figure 8:
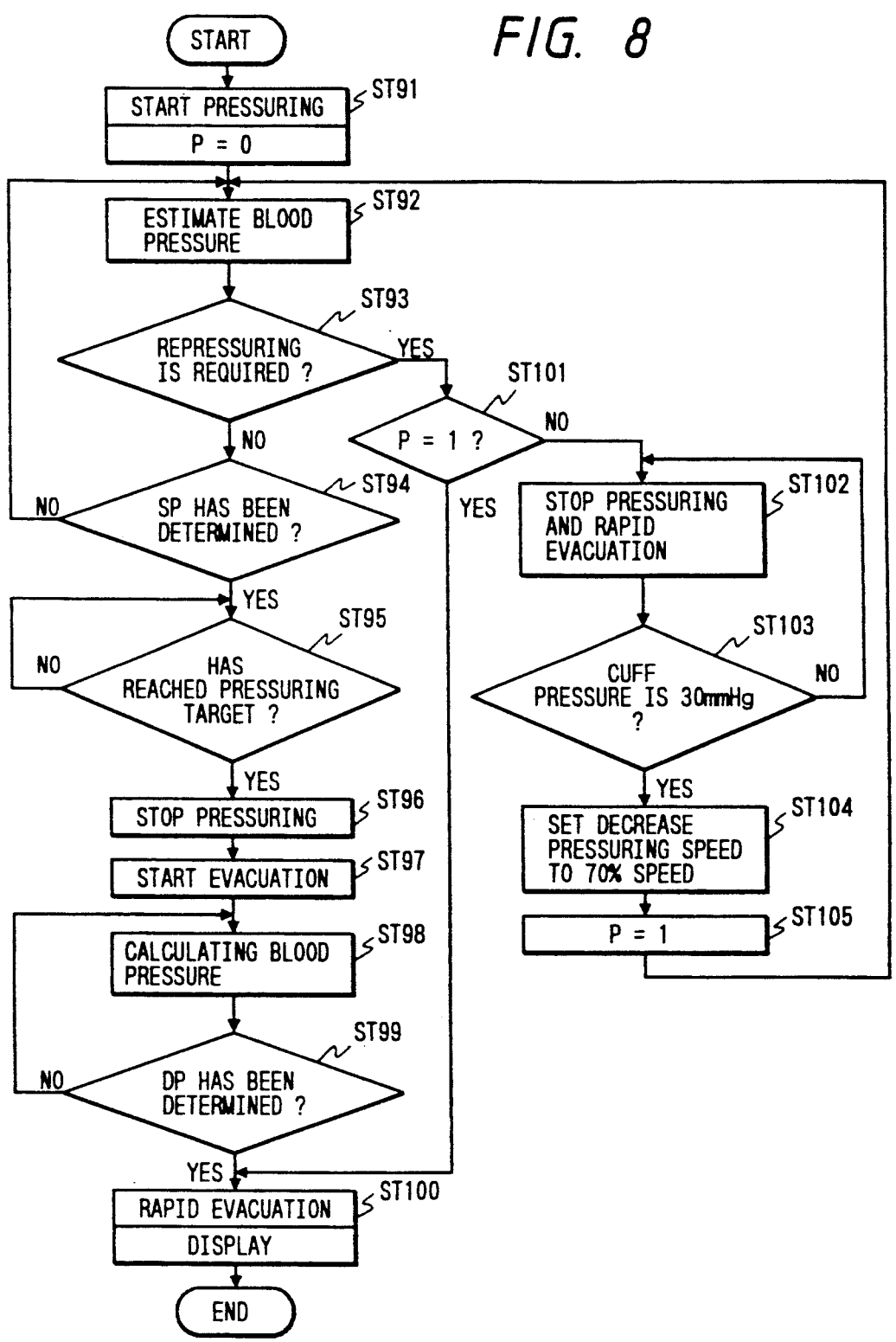
FIG. 8 is a flowchart showing an operation of an electronic blood pressure meter, according to a second embodiment of the invention.
Figure 9:
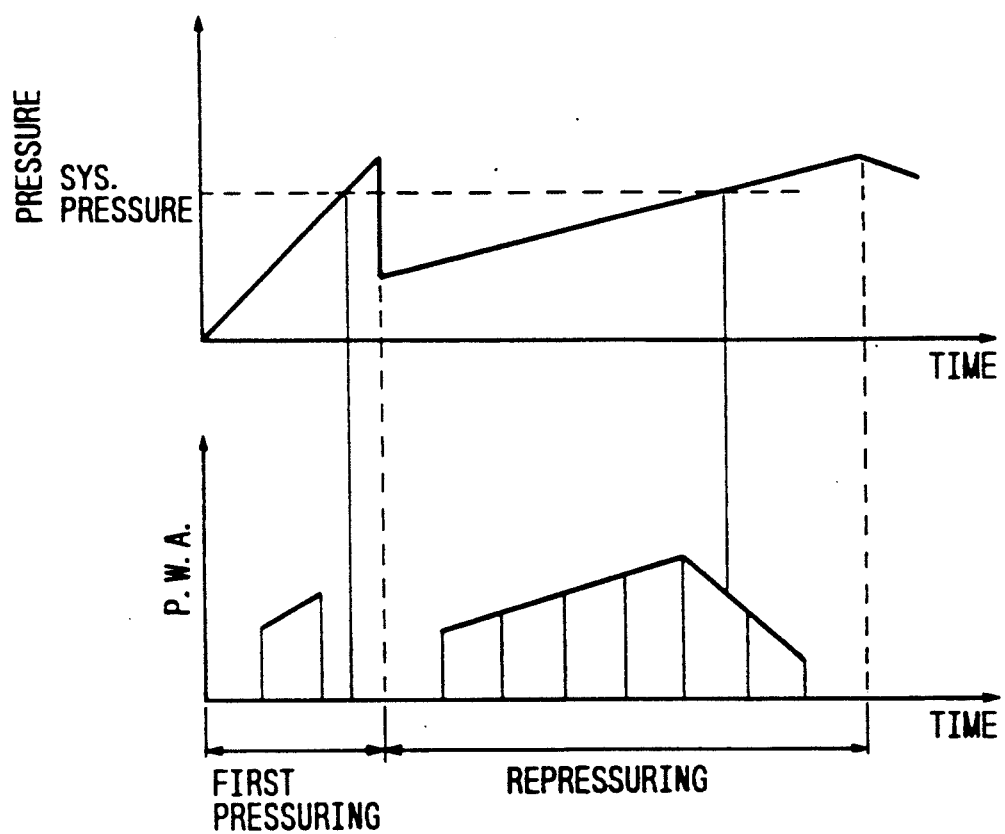
FIG. 9 is a diagram illustrative of a state in which a pressuring target is determined by the electronic blood pressure meter.

FIG. 8 is a flowchart showing a specific operation of the thus embodied electronic blood pressure meter. When the measurement switch has been pressed when the cuff 1 is wrapped around, e.g., a brachium, the pressuring pump 2 is driven to start pressuring the cuff 1. At this point, a repressuring operation identifying flag P is set to "0" at ST91. And during the cuff 1 pressuring process, the pulse wave information is detected (ST 92). In ST 93, it is determined whether or not the repressuring operation is needed. What is being judged here is whether or not the pulse wave information for estimating the maximum blood pressure has been detected; i.e., whether or not the pulse wave is not properly tracked due to the pressure speed being too fast when the cuff 1 is being pressured for a predetermined time and at a predetermined speed. If the pulse wave for estimating a maximum blood pressure is detected, no repressuring operation is necessary. Thus, "NO" is the result of ST 93, which causes the MPU to proceed to ST 94. In ST 94, whether or not an estimated maximum blood pressure value (SP) has been determined is judged. The MPU repeats ST 92 to ST 94 until the estimated maximum blood pressure value can be obtained. If it is assumed that the maximum blood pressure value is estimated now, then the result of ST 94 is "YES," and the MPU proceeds to ST 95. In ST 95, whether or not the cuff 1 has reached the pressuring target. In other words, whether or not the cuff 1 has been pressured to a value defined by adding, e.g., 15 mmHg to the estimated maximum blood pressure is judged. Supposing that the cuff 1 is pressured to reached the pressuring target, the judgment result in ST 95 becomes "YES," which then terminates the pressuring operation (ST 96). And the MPU proceeds to the cuff 1 evacuation process, and then a blood pressure calculating process for calculating maximum and minimum blood pressure values based on the pulse wave information obtained during this evacuation process is executed (ST 98). In ST 99, whether or not the maximum blood pressure value (DP) has been calculated. That is, whether or the maximum blood pressure value and the minimum blood pressure value have been determined is judged. When the maximum blood pressure value and the minimum blood pressure value have been determined, the result of ST 99 is "YES," causing the MPU to rapidly evacuate the cuff 1 and display the determined maximum and minimum blood pressure values on the display 9 (ST 100).

On the other hand, if it is judged that the repressuring operation is necessary in ST 93, i.e., because the arm of a subject is thin, etc., the cuff 1 pressuring speed is too fast and, as a result, the cuff pressure has already reached, e.g., a level of 180 mmHg, it is judged that pulse wave information required for estimating a maximum blood pressure has not been obtained, then the judgment result in ST 93 becomes "YES," which causes the MPU to proceed to ST 101. In ST 101, whether or not the repressuring operation identifying flag P is set to "1." In other words, whether not the repressuring operation has once been performed is judged. In this case, since it is a first repressuring operation and P is thus set to "0," the result in ST 101 becomes "NO," which not only causes the MPU to stop the cuff 1 pressuring operation but also to proceed to the rapid evacuation operation in ST 102. And in ST 103, whether or not the cuff pressure is decreased to 30 mmHg. That is, whether or not the cuff pressure is decreased to such an extent as to allow a pulse wave signal to be adequately detected. If the cuff 1 has been evacuated to a level of 30 mmHg, the result in ST 103 is "YES," which causes the MPU to start a repressuring operation with the cuff 1 pressuring speed successively set to 70% of the predetermined speed (ST 104). In other words, the pressuring speed is adjusted to such an extent as to allow a pulse wave signal to be tracked without fail even if the arm is too thin (see FIG. 9). At this point the repressuring operation identifying flag P is set to "1" (ST 105), and the MPU returns to ST 92 to perform the blood pressure estimating process at this pressuring speed, and the maximum blood pressure estimating process and the pressuring target determining process are similarly executed thereafter. The repressuring operation is performed only once in this embodiment, and if it is judged that the repressuring operation must be repeated (ST 93) after the first repressuring operation, then the MPU judging, e.g., that the cuff 1 wrapping condition is not satisfactory, returns from ST 101 to ST 100 to suspend the blood measurement.

While the example in which pulse wave information required for estimating a maximum blood pressure has ben obtained under the pressuring operation for a predetermined time and at a predetermined pressuring speed has been described as a criterion of whether a repressuring operation is necessary or not in the above embodiment, the application of the invention is not limited thereto. For example, it may be judged that a repressuring operation is required in the case no pulse wave is detected even if the internal pressure of the cuff 1 has reached a level of 140 mmHg, or in the case where no falling line of a pulse wave can be found even if the cuff 1 is pressured to 220 mmHg, or in similar cases.

As described in the foregoing description, the invention evacuates the cuff to a predetermined pressure and repressures it after reducing the cuff pressuring speed to a predetermined speed when a part of the pulse waves cannot be picked up and thus the estimated maximum blood pressure cannot be determined during the cuff pressuring operation. As a result, disadvantages such as not being able to determine a proper pressuring target due to the arm of a subject being thin, etc., which do not allow a maximum blood pressure to be estimated, can be eliminated. This contributes to determining the pressuring target quickly, easily, as well as surely. These are the advantages that the invention provides while achieving its object.

With the above described embodiments, the cuff evacuation in the blood pressure measurement is effected in a fixed, standardized manner by the predetermined slow speed evacuation (e.g., a 4 mmHg/s evacuation). However, in the third embodiment, the interval not essential for the blood pressure measurement (the interval between the timing after which the maximum blood pressure has been found and the timing at which the maximum pulse wave has been found) is substantially skipped by rapidly evacuating the cuff, so that the measurement time can be reduced, and the subject can thereby be relieved from pain caused by the pressure during the measurement.

The third embodiment of the present invention has circuit construction substantially same as that shown in FIG. 4.

In the third embodiment, the MPU 5 has the function of calculating a pulse wave amplitude value and determining a minimum blood pressure value and a maximum blood pressure value from the obtained pulse wave amplitude and cuff pressure values. The MPU 5 also has the function of estimating a cuff pressure and a maximum blood pressure at the time the extracted maximum pulse wave is present based on the pulse wave information obtained during the cuff pressuring process and storing the estimated pressure values in a memory. The MPU 5 further has the function of rapidly evacuating the cuff from a cuff pressure point defined by subtracting a predetermined value (15 mmHg) from the estimated maximum blood pressure value to a cuff pressure point defined by adding a predetermined value (15 mmHg) to the cuff pressure at the time the maximum pulse wave is present.

Further, the MPU 5 has the function of displaying the maximum and minimum blood pressure values on a display 10.

Figure 10A:
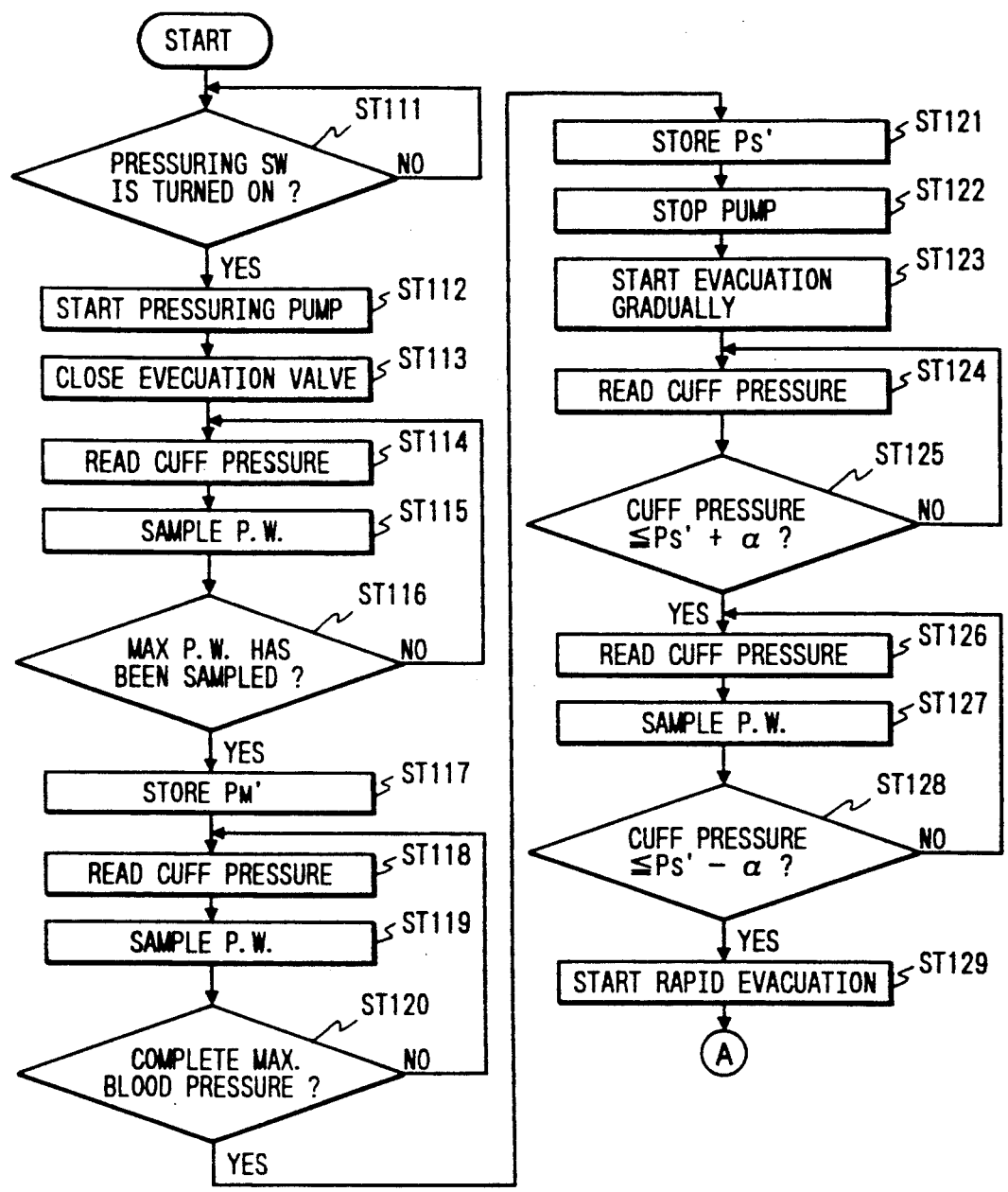
FIG. 10 (A) and 10 (B) are flowcharts showing specific operations of an electronic blood pressure meter, according to a third embodiment of the invention.

FIGS. 10 (A) and 10 (B) are flowcharts showing a specific operation of the thus embodied electronic blood pressure meter.

Figure 11:
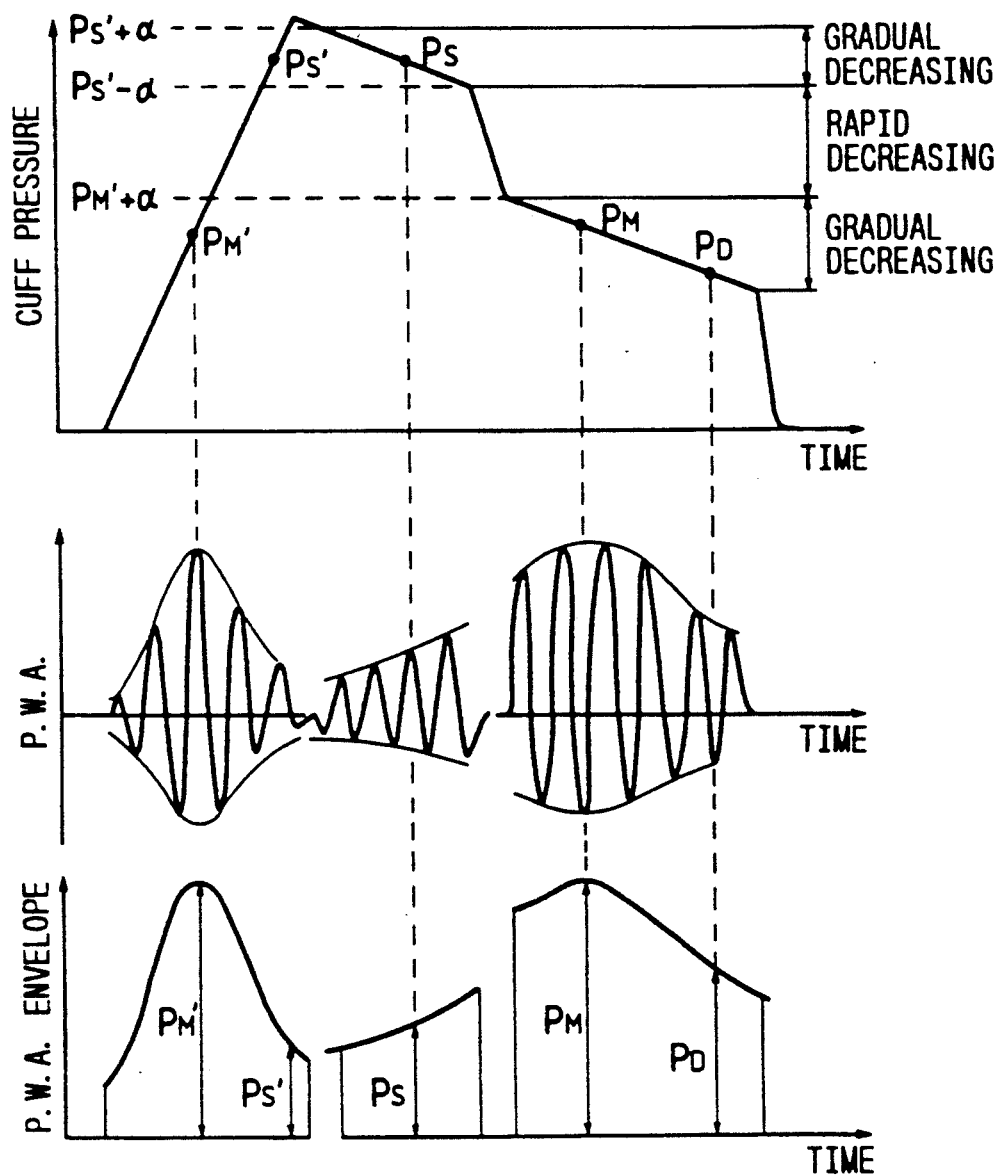
FIG. 11 is a diagram illustrative of the relationship between a cuff pressure and a pulse wave amplitude to indicate the state of measuring a blood pressure with the electronic blood pressure meter.

When a pressuring switch of the blood pressure meter is turned on (Step ST 111), the pressuring pump 2 is driven (ST 112). Simultaneously therewith, the control valve 3 is brought into a complete "closed" position (ST 113), and the cuff 1 gets rapidly pressured. While the cuff 1 is being thus pressured, not only the cuff pressure is read but also the pulse wave is extracted (ST 114 and ST 115). In ST 116, whether the maximum pulse wave has been extracted or not is judged. As shown in FIG. 11, when the maximum pulse wave (the pulse wave peak value) has been extracted at the rapid cuff pressuring stage, "YES" is the result in ST 116, which causes the CPU to store a cuff pressure $P_M'$ at the time the maximum pulse wave is present (see FIG. 11). The cuff pressure is continuously read and the pulse wave is extracted (ST 118 and ST 119). In ST 120, it is judged whether a maximum blood pressure value has been estimated or not. The maximum blood pressure is estimated as a pressure corresponding to a cuff pressure at the time 50% of the maximum pulse wave is present in its increasing phase. When the maximum blood pressure value $P_S'$ has been estimated, the result in ST 120 is "YES," which causes the MPU to store the estimated maximum blood pressure value $P_S'$ in the memory (ST 121). When the cuff 1 is pressured to reach a pressuring target, the operation of slowly evacuating the cuff 1 is started (ST 123) after the driving of the pressuring pump 2 has been stopped (ST 122). The slow evacuation of the cuff 1 is controlled by the control valve so as to be executed at a speed of about 4 mmHg/s. With the cuff being slowly evacuated, the cuff pressure is read (ST 124). In ST 125, it is judged whether or not the current cuff pressure is smaller than a pressure $(P_S' + \alpha)$ defined by adding a predetermined value $\alpha$ (15 mmHg) to the estimated maximum blood pressure. As shown in FIG. 11, when the cuff 1 is evacuated to cause the cuff pressure to be below this point, the result in ST 125 is "YES." This causes the CPU to read the cuff pressure and extract the pulse wave with the cuff being slowly evacuated (ST 126 and ST 127). And, in ST 128, it is judged whether or not the current cuff pressure is smaller than a value $(P_S' - \alpha)$ defined by subtracting a predetermined value $\alpha$ from the estimated maximum blood pressure. If the cuff 1 has been evacuated to have a value below this point, then the result in ST 128 is "YES," which causes the CPU to rapidly evacuate the cuff 1 (ST 129). In short, the cuff pressure and the pulse wave amplitude in a range ($\pm 15$ mmHG) around the maximum blood pressure value $P_S'$ that is roughly estimated during the process of pressuring the cuff 1 are detected to find a genuine $P_S$ (a pulse wave that is a value 50% of the maximum pulse wave and a cuff pressure corresponding to such pulse wave), and the cuff 1 is rapidly evacuated thereafter.

Figure 10B:
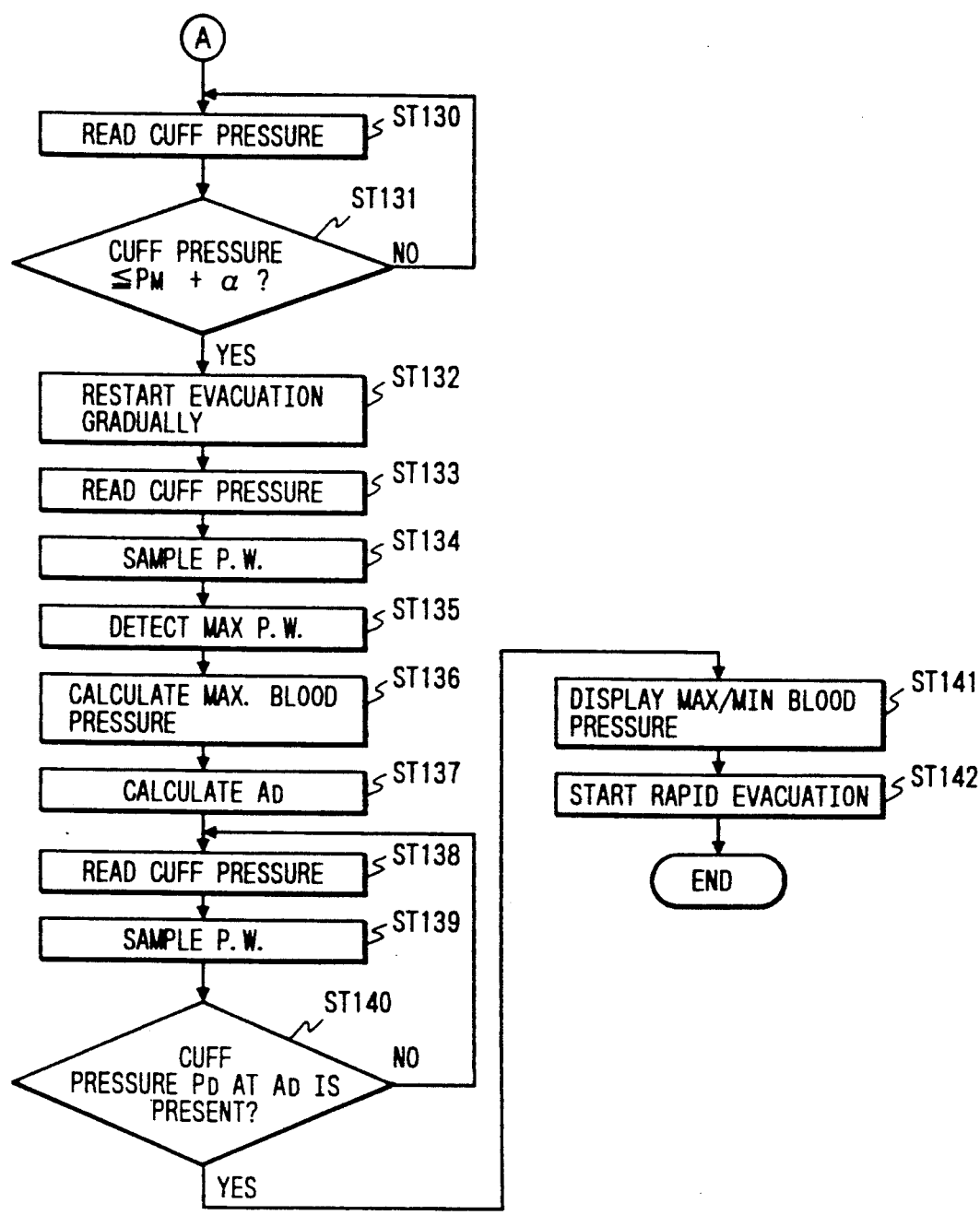

And as shown in FIG. 10(B), during the process of rapidly evacuating the cuff I, a cuff pressure is being read (ST 130). In ST 131, it is judged whether or not the cuff pressure has been below a value ($P_M' + \alpha$) defined by adding a predetermined value o to the cuff pressure $P_M'$ at the time the maximum pulse wave is present. In other words, it is judged whether or not the cuff pressure has neared at a point where the maximum pulse wave is present. As shown in FIG. 11, when the pressure of the cuff 1 has dropped to the point ($P_M' + \alpha$), the result in ST 131 is "YES." which causes the CPU to suspend the rapid evacuation by the control value 3 and the cuff 1 is thereby subjected to a slow evacuation again (ST 132). While the cuff is being slowly evacuated, the cuff pressure is being read and the pulse wave is being extracted (ST 133 and ST 134) to detect a maximum pulse wave $A_M$ (ST 135). A value $A_S$ (a pulse wave amplitude at the time of SYS) is calculated from $A_M$ by a predetermined operation, and the cuff pressure (larger than a cuff pressure at the time $A_M$ is present) at the time $A_S$ is present is calculated as a maximum blood pressure (ST 136). Further, $A_M$ is subjected to predetermined processing to obtain $A_D$ (a pulse wave amplitude at the time of DIA) (ST 137). Then, the cuff is being read and the pulse wave is being extracted (ST 138 and ST 139). In ST 140, it is judged whether or not the cuff pressure $P_D$ at the time $A_D$ that has been calculated in ST 137 is present (see FIG. 11), i.e., the minimum blood pressure, has been stored is judged. If the minimum blood pressure has been stored, and if the minimum blood pressure has been stored, then the result in ST 140 is "YES." This causes the CPU to display the maximum blood pressure and the minimum blood pressure on the display 9 (ST 141), and the cuff 1 is thereafter subjected to rapid evacuation (ST 142).

As described in the foregoing, the invention estimates both the cuff pressure and the maximum blood pressure at the time the maximum pulse wave is present based on the pulse wave information obtained during the cuff pressuring process, and then rapidly evacuates the cuff from the cuff pressure point defined by subtracting a predetermined value from the estimated maximum blood pressure to the cuff pressure point defined by adding a predetermined value to the cuff pressure at the time the maximum pulse wave is present during the cuff evacuating process. Therefore, the interval that is not essential to the measurement, i.e., an interval between the timing after which the maximum blood pressure is present to the timing at which the maximum wave pulse is present, can be skipped by rapidly evacuating the cuff. Hence, the wasteful interval can be eliminated from the measurement, which contributes not only to achieving a reduction in measurement time, but also to making a measurement without keeping the subject under pain for a long time. Further, since the reduction in measurement time leads to a reduction in the rate of mixture of noise such as body movements, thereby allowing the reliability in measurement accuracy to be improved. Such advantages are provided by the invention by successfully achieving its object.

What is claimed is:

1. An electronic blood pressure meter comprising:

a cuff;

cuff pressure control means for controlling an inside fluid pressure of said cuff;

means for detecting said inside fluid pressure of said cuff to produce a cuff pressure detecting signal;

means for extracting a pulse wave component superposed on said cuff pressure detecting signal during pressure control operations performed by said cuff during pressure control operations performed by said cuff pressure control means;

means for calculating an amplitude of said pulse wave component extracted by said pulse wave extracting means;

means for determining a blood pressure during an evacuating operation of said cuff pressure control means based on output signals of said amplitude calculating means and said pressure detecting means; and maximum blood pressure estimating means for obtaining an estimated value of a maximum blood pressure in response to output signals of said pulse wave extracting means and said pressure detecting means while said cuff is being pressurized by said cuff pressure control means, said cuff pressure control means stopping pressurization of said cuff when said inside fluid pressure of said cuff exceeds a total pressure of said estimated value and a predetermined value, wherein said maximum blood pressure estimating means detects a maximum in said pulse wave amplitude extracted while said cuff is being pressurized by said cuff pressure control means to determine a threshold value, and said maximum pressure estimating means determined, as said estimated value, said inside pressure of said cuff when said pulse wave amplitude is less than said threshold value.

2. The electronic blood pressure meter, as defined in claim 1, wherein said threshold value is determined by said maximum blood pressure determining means as one-half of the maximum pulse wave amplitude.

3. The electronic blood pressure meter, as defined in claim 1, wherein said cuff pressure control means stops pressurization when said inside fluid pressure of the cuff exceeds said estimated value by 30 mmHg.

* * * * *